(12) United States Patent
Beard et al.

(10) Patent No.: US 9,833,346 B2
(45) Date of Patent: Dec. 5, 2017

(54) DEPLOYMENT HANDLE FOR A MEDICAL DEVICE DEPLOYMENT SYSTEM

(71) Applicant: W. L. Gore & Associates, Inc., Newark, DE (US)

(72) Inventors: Matthew S. Beard, Phoenix, AZ (US); David A. Herrin, Seattle, WA (US); Joseph N. Kennelly Ullman, Seattle, WA (US); Martin J. Sector, Gilbert, AZ (US); Justin W. Sokel, Flagstaff, AZ (US); Jared L. Van Cleave, Kirkland, WA (US)

(73) Assignee: W. L. Gore & Associates, Inc., Newark, DE (US)

( * ) Notice: Subject to any disclaimer, the term of this patent is extended or adjusted under 35 U.S.C. 154(b) by 179 days.

(21) Appl. No.: 14/670,234

(22) Filed: Mar. 26, 2015

(65) Prior Publication Data

US 2015/0282964 A1  Oct. 8, 2015

Related U.S. Application Data

(60) Provisional application No. 61/975,165, filed on Apr. 4, 2014.

(51) Int. Cl.
*A61F 2/95* (2013.01)
*A61F 2/966* (2013.01)

(52) U.S. Cl.
CPC .............. *A61F 2/95* (2013.01); *A61F 2/966* (2013.01); *A61F 2002/9517* (2013.01)

(58) Field of Classification Search
CPC .. A61F 2/95; A61F 2/962; A61F 2/966; A61F 2002/0072; A61F 2002/011; A61F 2002/2466; A61F 2002/2484; A61F 2002/9517; A61F 2002/954; A61F 2002/9665; A61F 5/0089; A61M 25/0062; A61M 2025/0681

See application file for complete search history.

(56) References Cited

U.S. PATENT DOCUMENTS

| 5,707,376 A | 1/1998 | Kavteladze et al. |
| 5,776,141 A | 7/1998 | Klein et al. |
| 5,782,909 A | 7/1998 | Quiachon et al. |

(Continued)

FOREIGN PATENT DOCUMENTS

WO   03/068302   8/2003

OTHER PUBLICATIONS

International Search Report and Written Opinion for PCT/US2015/023140 dated Aug. 7, 2015, corresponding to U.S. Appl. No. 14/670,234, 5 pages.

*Primary Examiner* — Todd J Scherbel (57) ABSTRACT

An introducer assembly includes a first actuating mechanism for actuating a constraining sheath between a first state releasably constraining a vascular implant and a second state allowing deployment of the vascular implant; a second actuating mechanism for actuating a blocking mechanism between a blocked state for blocking other functions of the handle and an unblocked state for allowing operation of the other functions of the handle; and an operating knob operatively coupled to both of the first and second actuating mechanisms for concurrent operation of both of the first and second actuating mechanisms in response to actuation of the operating knob.

21 Claims, 9 Drawing Sheets

(56) References Cited

U.S. PATENT DOCUMENTS

| | | |
|---|---|---|
| 5,906,619 A | 5/1999 | Olson et al. |
| 6,143,021 A | 11/2000 | Staehle |
| 6,352,561 B1 | 3/2002 | Leopold et al. |
| 6,383,211 B1 | 5/2002 | Staehle |
| 6,527,779 B1 | 3/2003 | Rourke |
| 6,551,350 B1 | 4/2003 | Thornton et al. |
| 6,743,210 B2 | 6/2004 | Hart et al. |
| 6,755,854 B2 | 6/2004 | Gillick et al. |
| 6,866,669 B2 | 3/2005 | Buzzard et al. |
| 6,884,259 B2 | 4/2005 | Tran et al. |
| 6,926,732 B2 | 8/2005 | Derus et al. |
| 6,939,352 B2 | 9/2005 | Buzzard et al. |
| 7,033,368 B2 | 4/2006 | Rourke |
| 7,052,511 B2 | 5/2006 | Weldon et al. |
| 7,066,951 B2 | 6/2006 | Chobotov |
| 7,122,050 B2 | 10/2006 | Randall et al. |
| 7,198,636 B2 | 4/2007 | Cully et al. |
| 7,208,003 B2 | 4/2007 | Davis et al. |
| 2005/0027305 A1 | 2/2005 | Shiu et al. |
| 2005/0080476 A1* | 4/2005 | Gunderson .............. A61F 2/95 623/1.11 |
| 2010/0049293 A1 | 2/2010 | Zukowski et al. |
| 2015/0230816 A1* | 8/2015 | Strobl ............... A61B 17/3201 606/45 |

* cited by examiner

DEPLOYMENT HANDLE FOR A MEDICAL DEVICE DEPLOYMENT SYSTEM

BACKGROUND

Field

The present disclosure relates to medical device deployment systems. More particularly, the present disclosure relates to a handle for a medical device deployment system.

Discussion of the Related Art

There is a need for advanced devices, tools, systems and methods used for the endoluminal treatment of aortic diseases. In particular, there remains a need for deployment systems that can accommodate increasingly complex modes of deployment of a device, such as steering, reconstraining, multiple stage deployment, multiple device deployment, while promoting ease of use to the clinician.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

DETAILED DESCRIPTION

Introducer assemblies for endoluminal delivery of vascular implants in accordance with various embodiments are disclosed for allowing actuation or deployment of a vascular implant, while forcing a particular order of operation of the handle by a clinician.

Figure 1:
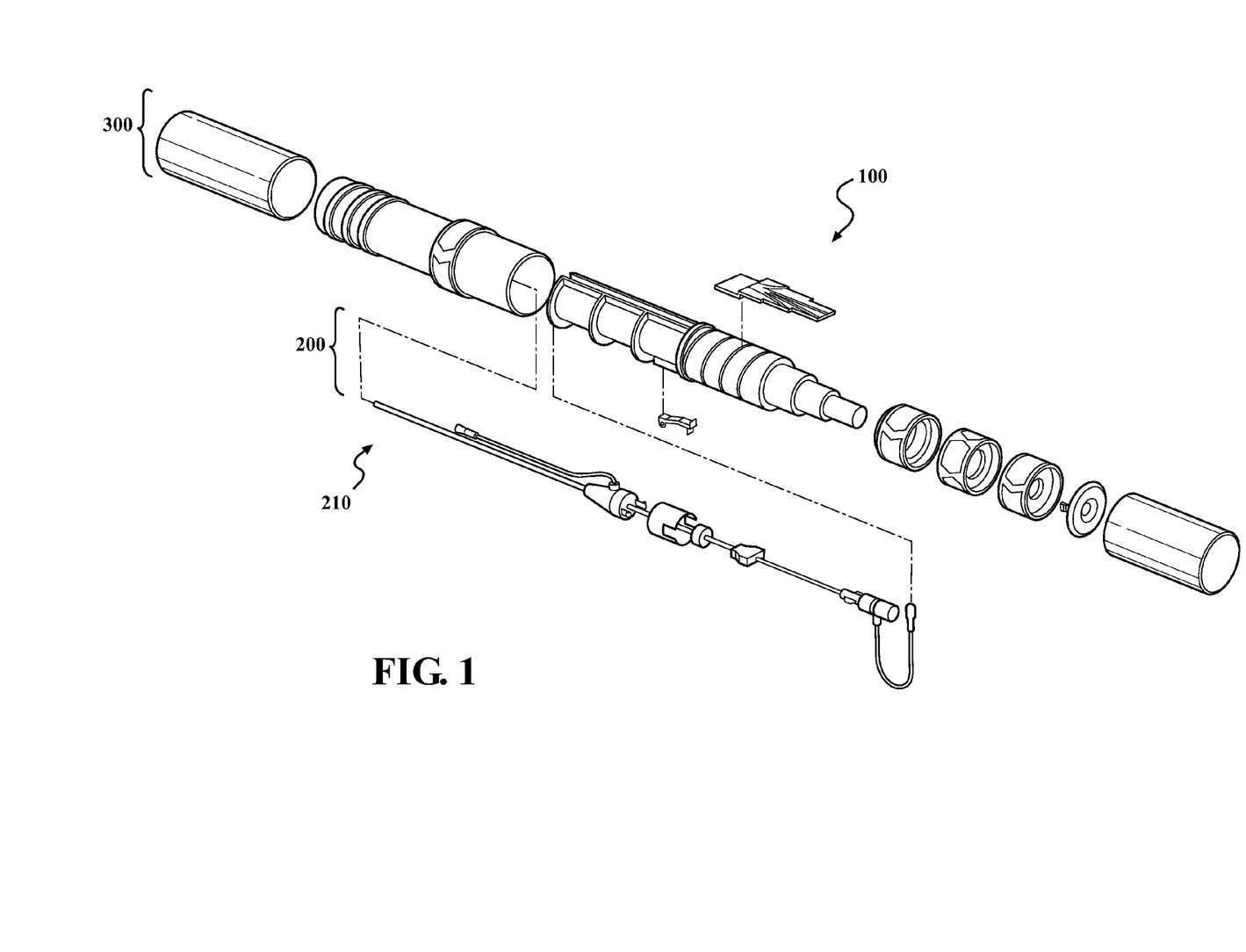
FIG. 1 is an exploded perspective view of an introducer assembly in accordance with the present disclosure.

In various embodiments, an introducer assembly includes a first actuating mechanism for actuating a constraining sheath between a first state releasably constraining a vascular implant and a second state allowing deployment of the vascular implant; a second actuating mechanism for actuating a blocking mechanism between a blocked state for blocking one or more other knobs and/or other functions of the handle and an unblocked state for allowing operation of the one or more other knobs and/or other functions of the handle; and an operating knob operatively coupled to both of the first and second actuating mechanisms for concurrent operation of both of the first and second actuating mechanisms in response to actuation of the operating knob. An example of such an introducer assembly is generally indicated at 100 in FIG. 1. The introducer assembly 100 includes a sheath 200 and a handle 300. The introducer assembly 100 includes a constraint (not shown) for releasably constraining a vascular implant toward a distal end 210 of the sheath 200. The constraint has a first state releasably constraining an expandable implant toward a delivery configuration suitable for endoluminal delivery, and a second state released to allow expansion of the implant from the delivery configuration toward a deployed configuration. The handle includes an actuating member operatively coupled to the constraint for actuating the constraint between the first state and the second state.

In various embodiments, the constraint can include a film sleeve that extends around the implant. In the first state, opposite portions or edges of the film sleeve can be releasably held or sewn together by an elongated member, such as a wire or fiber, to maintain the implant in the delivery configuration. In such embodiments, the sleeve can be opened, or otherwise disrupted, by displacing, unstitching or otherwise disengaging the elongated member from the film sleeve to allow expansion of the implant. Further details of such constraining sleeves can be found, for example, U.S. Pat. No. 6,352,561 issued to Leopold, et al., and U.S. Pat. No. 6,551,350 issued to Thornton, et al., the content of which is incorporated herein by reference in its entirety. In such embodiments, the actuating member can be coupled to the elongated member to release or open the film sleeve from the first state to the second state.

In other embodiments, the constraint can include an axially displaceable tube, wherein such a tube can be formed from a wrapped film tube or an extruded polymer. Indeed, in various embodiments, the sheath itself could be such a constraint, wherein the sheath in the first state extends over the implant to retain the implant toward the delivery configuration. The sheath can be displaced toward the second state to allow expansion of the implant from the delivery configuration. In such embodiments, the actuating member can be coupled to the sheath so that the sheath is displaced with the actuating member between the first state and second state.

Thus, the actuating member can be configured for deploying an implant from either type of constraint described above, or other similarly actuated constraint mechanisms known in the art. The latter type of integrated sheath and constraint are described below in connection with the illustrated embodiments.

Referring to FIGS. 9A-9D, the handle 300 includes an actuating member 310 coupled to the sheath 200 for actuating the sheath 200 between the first state and second state in response to linear displacement of the actuating member 310 between a first position and a second position, respectively. The handle 300 includes a first actuating mechanism 320 for displacing the actuating member 310 between the first position and the second position.

Figure 9A:
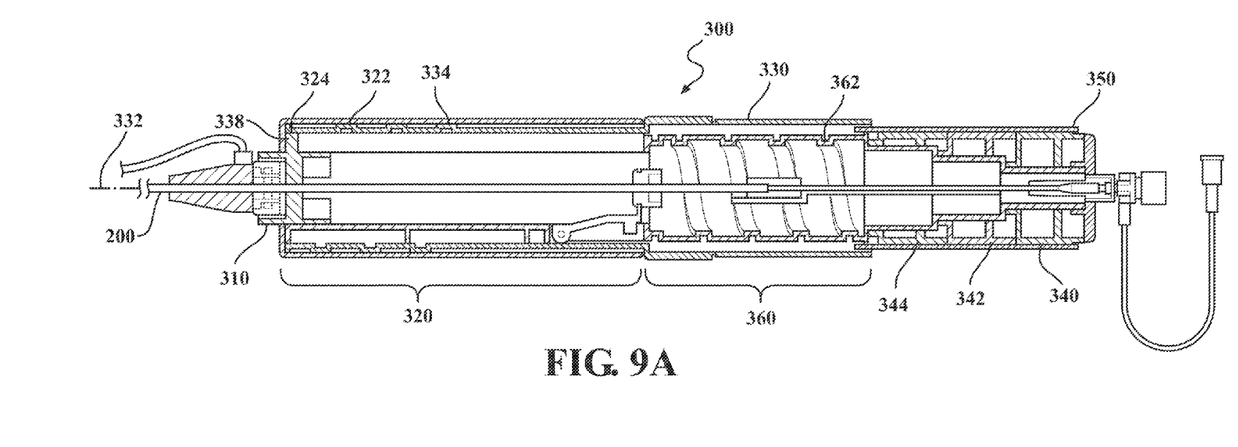
FIGS. 9A and 9B are top and front elevational views, respectively, of a handle of the introducer assembly in a first state.
Figure 9B:
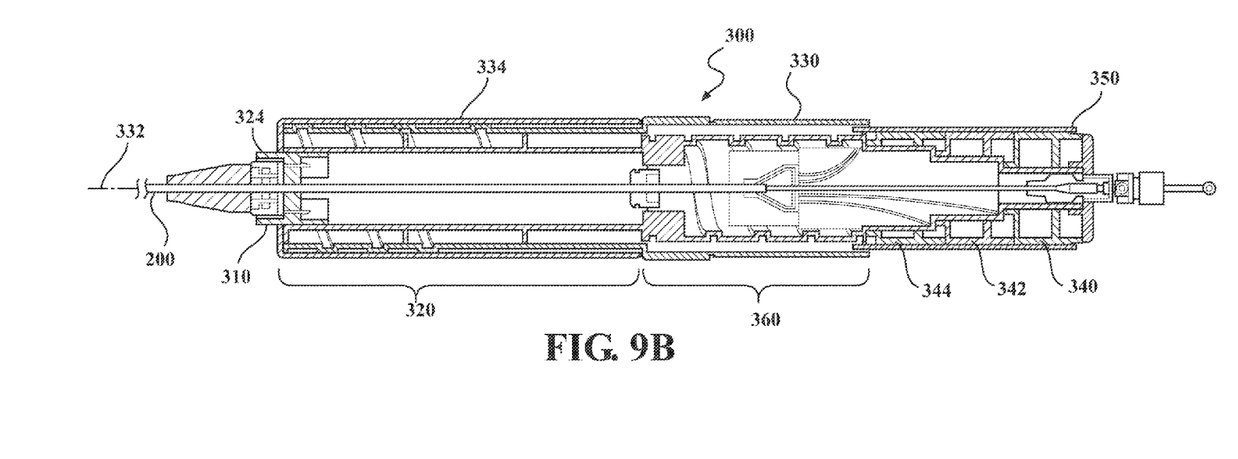
Figure 9C:
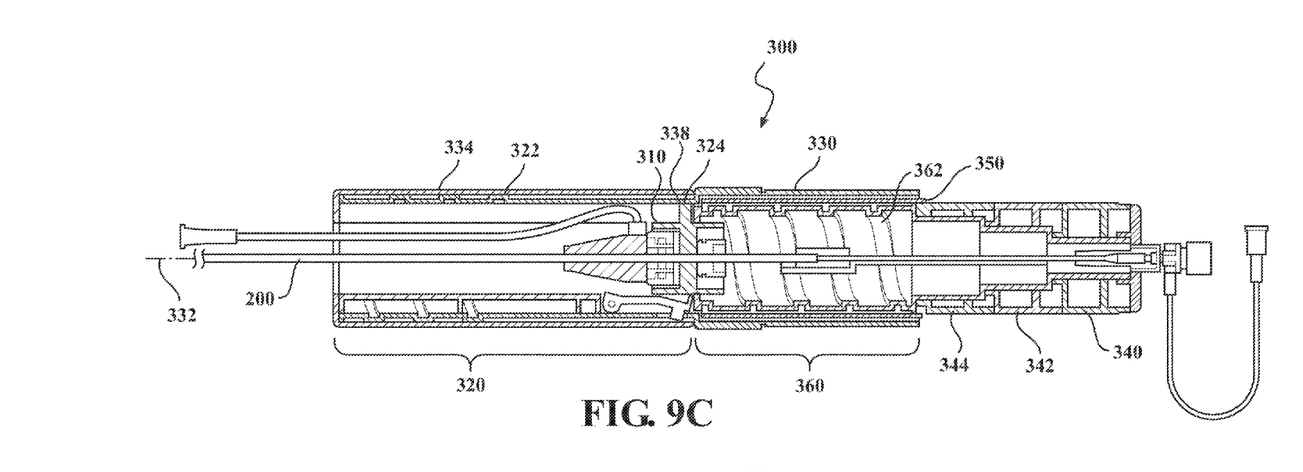
FIGS. 9C and 9D are top and front elevational views, respectively, of a handle of the introducer assembly in a second state.
Figure 9D:
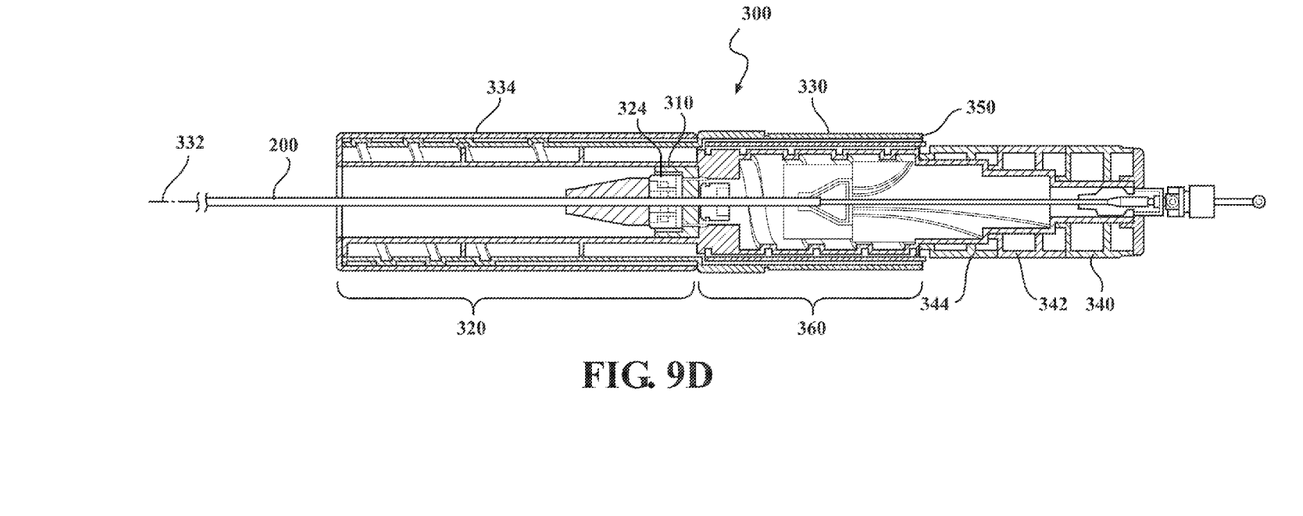

The handle 300 includes a main knob 330 for operating the first actuating mechanism 320. Described further below, the handle 300 can include one or more additional knobs to operate one or more additional separate handle functions. The handle 300 includes a cover 350 operable for movement between a covered state covering the one or more additional knobs 340, 342, 344 as shown in FIGS. 9A and 9B, and an uncovered state allowing access to the one or more additional knobs 340, 342, 344 as shown in FIGS. 9C and 9D. The handle 300 includes a second actuating mechanism 360 for displacing the cover 350 between the covered state and the uncovered state. The main knob 330 is operatively coupled to both of the first actuating mechanism 320 and the second actuating mechanism 360 to cause displacement of both the actuating member 310 between the first state and the second state and the cover 350 between the covered state and the uncovered state, respectively, in response to corresponding operation of the main knob 330.

Figure 10:
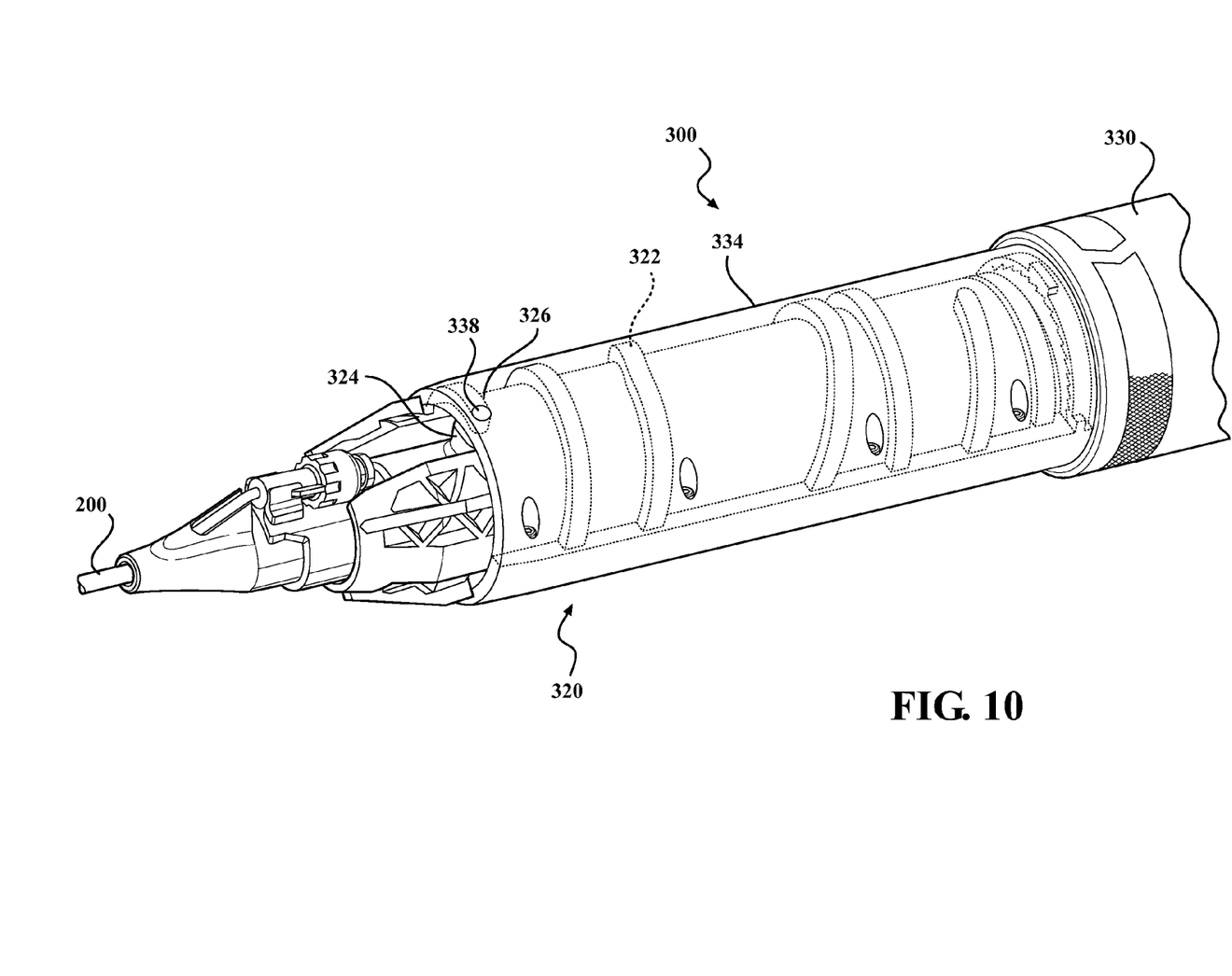
FIG. 10 is a perspective view of a front portion of the introducer assembly.
Figure 11:
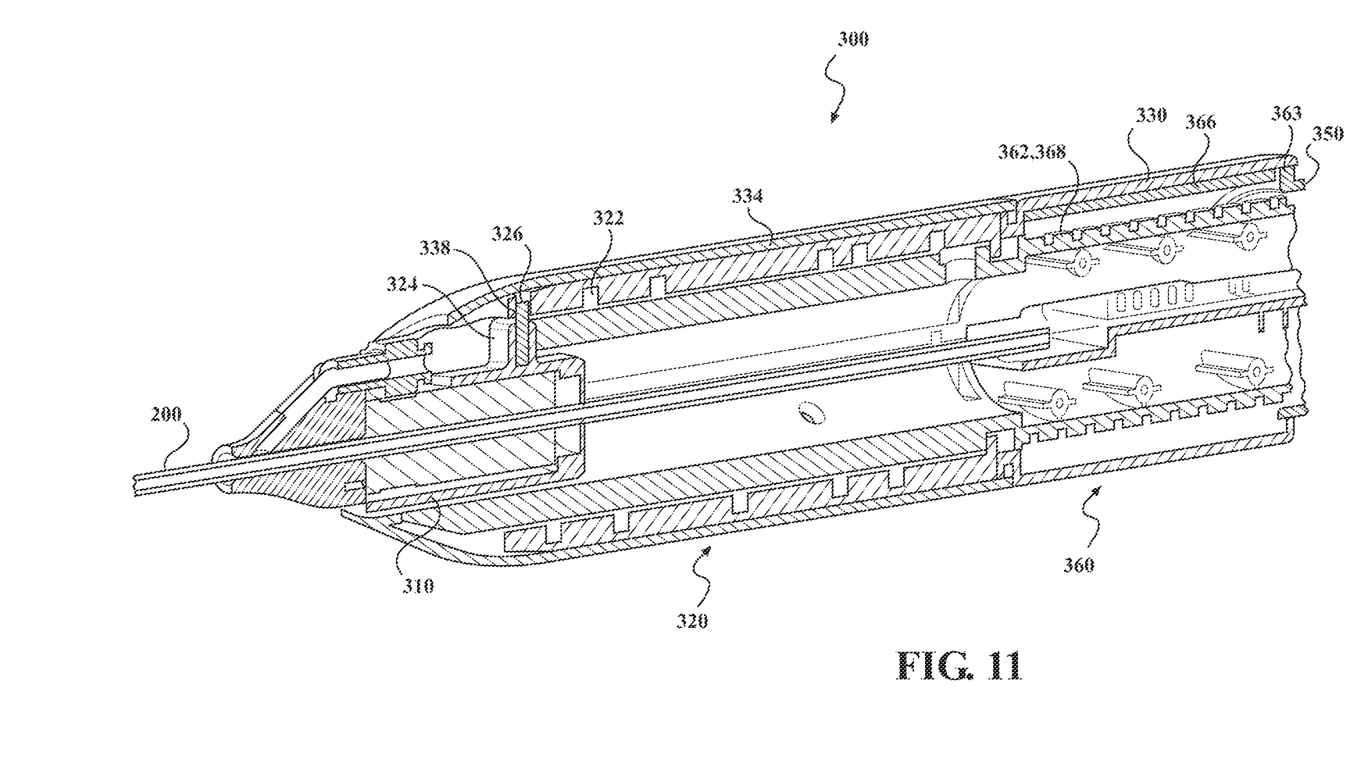
FIG. 11 is a cross-sectional view of a front portion of the introducer assembly.

In various embodiments, an actuating knob of the handle can be configured for rotation about an axis, and an actuating member for actuating one or more functions of the handle can be configured for displacement along and/or about the axis between operating states in response to corresponding rotation of the actuating knob. For example, as shown in FIGS. 9A-9D, the main knob 330 is rotatable about a rotational axis 332. The actuating member 310 is movable linearly along the axis 332 between the first state and second state. Referring to FIGS. 10 and 11, the first actuating mechanism 320 includes a first helical guide 322 movable with the main knob 330 about the axis 332. The first actuating mechanism 320 includes a first follower 324 on the actuating member 310 engaged with the first helical guide 322 to cause linear movement of the actuating member 310 between the first state and second state in response to corresponding rotation of the main knob 330. The main knob 330 includes a receiving tube 334 receiving at least a portion of the actuating member 310 therethrough as the actuating member 310 moves between the first state and second state. In a number of embodiments, for example as shown in FIGS. 10-11, the first helical guide 322 is a first helical slot 326 formed along an inner surface 336 of the receiving tube 334 and the first follower 324 includes an outwardly extending first pin 338 engaged with the helical slot 326.

Figure 12:
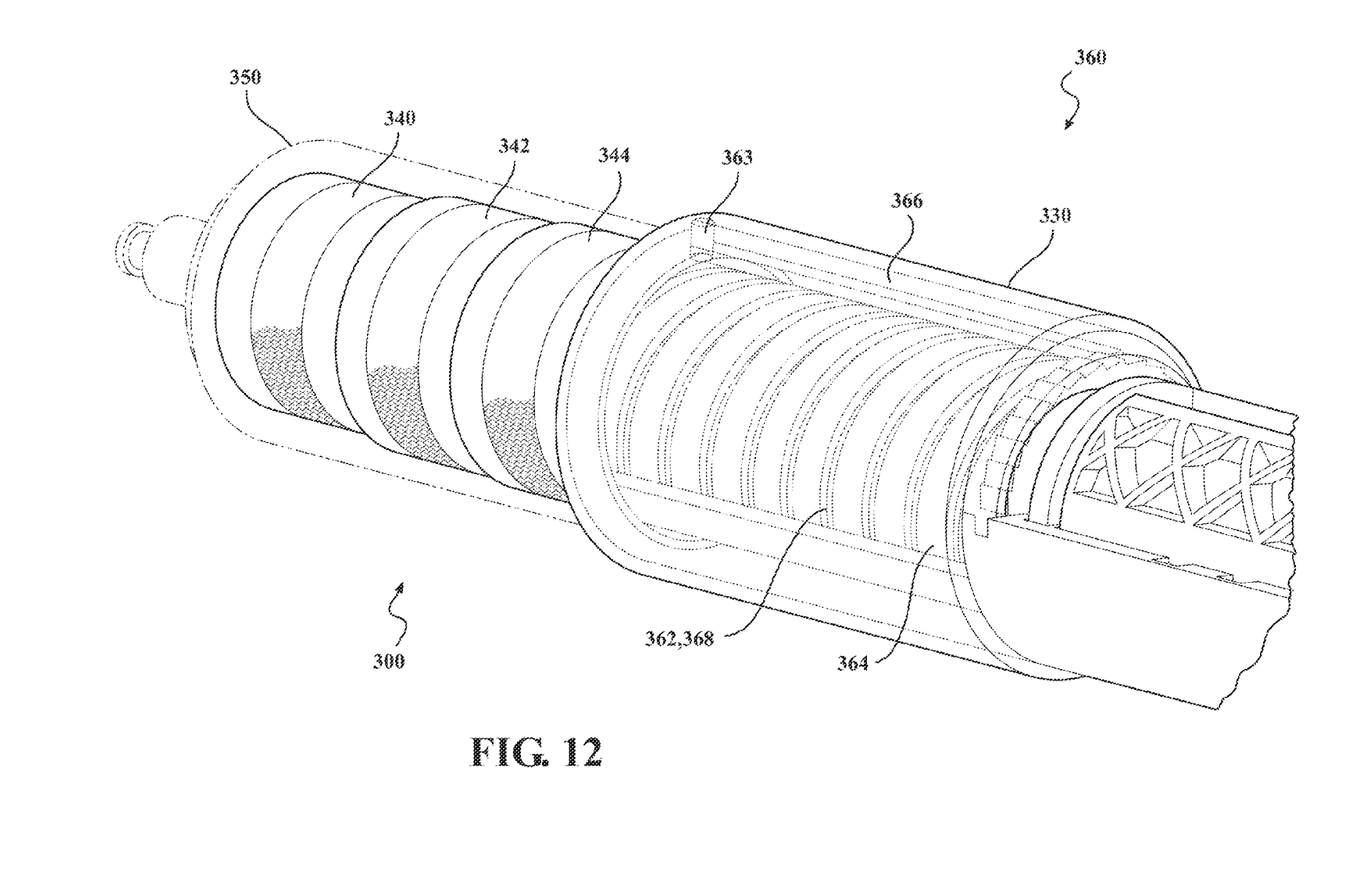
FIG. 12 is a perspective view of a rear portion of the introducer assembly.
Figure 13:
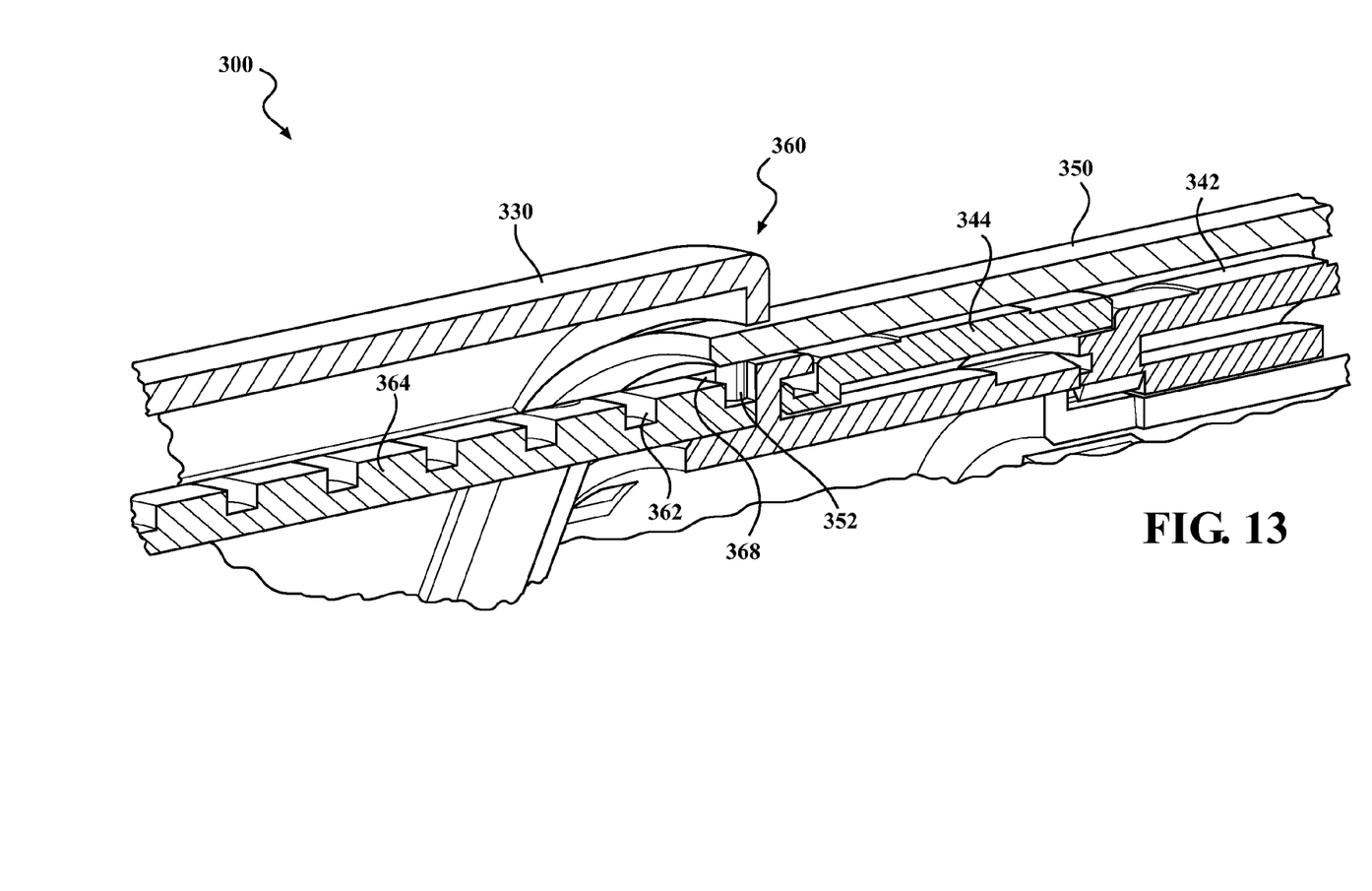
FIG. 13 is a cross sectional view of a rear portion of the introducer assembly.

Referring to FIG. 12, the second actuating mechanism 360 includes a second helical guide 362 that translates rotation of the main knob 330 to axial displacement of the cover 350. In one embodiment, the second helical guide 362 comprises a second helical slot 368 formed along an outer surface 366 of a spindle 364, the spindle 364 being aligned with the axis 332 (FIG. 9A-9D) of the main knob 330. The second actuating mechanism 360 also includes a longitudinal slot 366 formed along the main knob 330. In various embodiments, the slot 366 is parallel with the axis 332 of the main knob 330. The second actuating mechanism 360 includes a second pin 363 extending from the cover 350 and slidably engaged with the longitudinal slot 366. As best shown in FIG. 13, the second actuating mechanism 360 includes a third pin 352 extending from the cover 350 and engaging the second helical slot 368 to cause displacement of the cover 350 between the covered state and the uncovered state in response to corresponding rotation of the main knob 330.

The actuating mechanisms of the handle can be configured so that functions, such as displacements of the actuating member and cover, are delayed or accelerated relative to each other during operation of the main knob. For example, the first helical guide can include a flat or reduced or increased pitch to cause a delay, decrease or increase, respectively, in the displacement of the actuating mechanism relative to the cover in response to operation of the main knob.

In various embodiments, the handle can include a ratchet mechanism that allows actuation of an actuating knob in a first direction and prevents rotation of the actuating knob in an opposite second direction. For example, the handle can include a ratchet mechanism having a gear rack on the main knob and a fixed pawl that engages the gear rack to allow rotation of the main knob in a first direction as the pawl slips along teeth of the gear rack and that limits rotation of the main knob in an opposite second direction as the pawl catches a tooth on the gear rack. The pawl can be a spring-loaded machined component or alternatively, the pawl can be formed from spring leaf metal. The pawl can be configured to generate audible noise and/or at least provide tactile feedback as the pawl slips along the teeth of the gear rack. Optionally, one or more of the teeth of the gear rack can be sized and/or shaped differently from the other teeth of the gear rack to cause a distinct change in sound, e.g. pitch, or tactile feedback, e.g. clicks, resistance, that indicates to a clinician when a certain step in the deployment is achieved.

Figure 2:
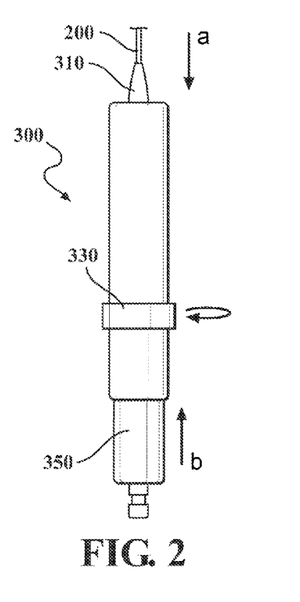
FIGS. 2-8 illustrate various states of a handle of the introducer assembly of FIG. 1.

In use, rotation of the main knob 330 about the axis 332 simultaneously operates the first actuating mechanism 320 to cause displacement of the actuating member 310 in a first direction, as indicated at arrow "a" in FIG. 2, and the second actuating mechanism 360 to cause displacement of the cover 350 in a second direction, as indicated at arrow "b" in FIG. 2. Displacement of the actuating member 310 in the first direction "a" causes corresponding displacement of the sheath 200 to allow expansion of the expandable implant 400 outwardly from the delivery configuration. The expandable vascular implant can be a self-expanding stent graft or, alternatively, a balloon-expanded implant. Displacement of the cover 350 in the second direction "b" can reveal one or more additional knobs each for operating one or more other handle functions.

Figure 3:
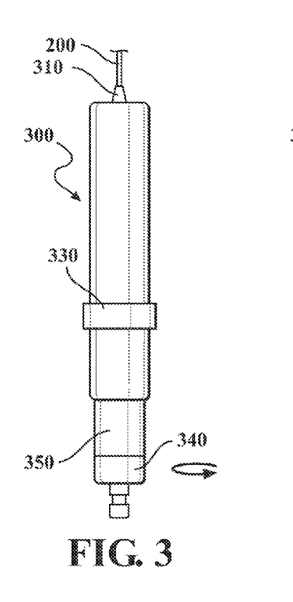

For example, as illustrated in FIG. 3, a second knob 340 is revealed after displacement of the cover 350 for operating a constraining mechanism for selectively constraining at least a portion of the implant to allow positioning of the device prior to committing to a full deployment of the implant at the treatment site. A detailed description of constraining mechanisms, construction and methods of use of such constraining mechanisms are provided in co-pending application U.S. Patent Application Publication US 2010/0049293 A1 (Zukowski et al.), the content of which is incorporated herein by reference in its entirety.

In various embodiments, the handle can be configured so that the cover can be displaced in steps to reveal additional knobs each for operating one or more other handle functions.

Figure 4:
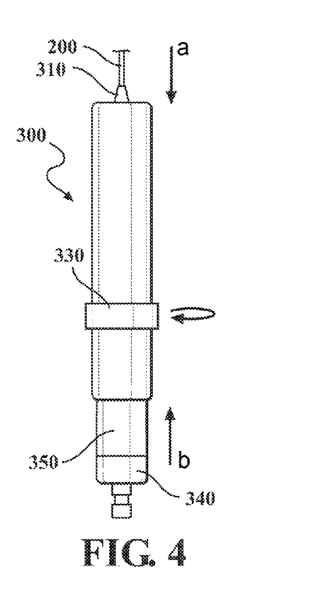
Figure 5:
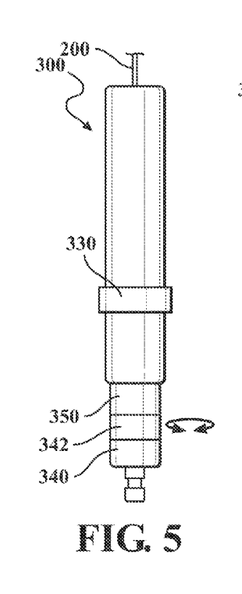

Continued rotation of the main knob 330, for example, as illustrated in FIG. 4, causes further displacement of the cover 350 in the second direction "b" to reveal a third knob 342, as shown in FIG. 5. The third knob 342 can be configured to actuate one or more other handle functions, such as displacing fibers, wires, levers, gears or any combination thereof of a steering mechanism (not shown) for selectively bending or otherwise steering at least a portion of the implant 400 during deployment.

Figure 6:
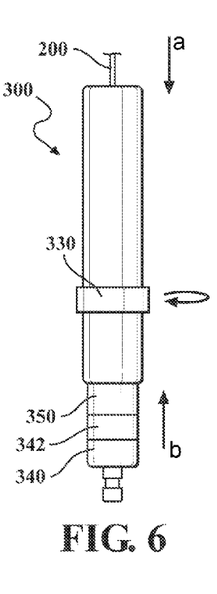
Figures 7, 8:
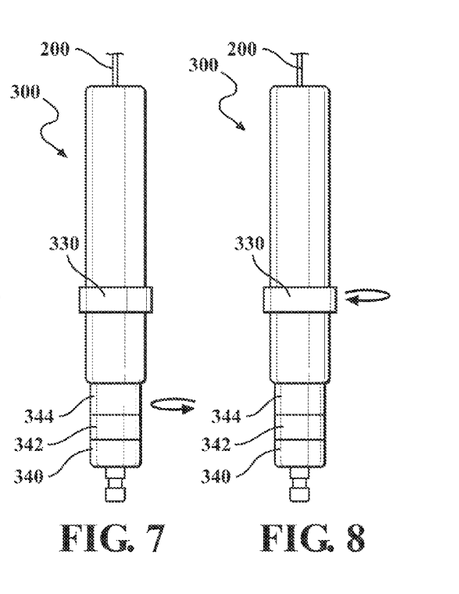

Continued rotation of the main knob 330, for example, as illustrated in FIG. 6, causes further displacement of the cover 350 in the second direction "b" to reveal a fourth knob 344, as shown in FIGS. 7-8. The fourth knob 344 can be configured to actuate one or more other handle functions, such as displacing fibers, wires, levers, gears or any combination thereof of a release mechanism. In one embodiment, a release mechanism can include a lock wire frictionally engaged with the implant to maintain a releasable coupling between the implant and the handle. The lock wire can be operatively coupled to the fourth knob to be displaced relative to and disengaged from the implant in response to actuation of the fourth knob. For example, the lock wire can be wound about a spindle portion of the fourth knob during rotation of the fourth knob. Winding of the lock wire about the spindle displaces the lock wire relative to the implant until the lock wire disengages from the implant.

In various embodiments, handle functions, such as steering, reconstraining, and deploying of an expandable implant can be operated by actuating the one or more knobs of the handle, while maintaining the implant at an intermediate configuration within a secondary or intermediate sheath or sleeve, wherein the intermediate configuration is larger than the delivery configuration and smaller than a deployed configuration. For example, the introducer assembly can include a secondary sheath for limiting expansion of the implant to an intermediate configuration after displacement of the constraining sheath. The secondary sheath can include a flexible film constraining sleeve that extends over and releasably constrains the implant. An elongated coupling member, such as a fiber or wire, stitches opposing edges or sides of the constraining sleeve together to releasably constrain the implant toward the intermediate configuration. The constraining sleeve can be opened by de-coupling the coupling member from the constraining sleeve. Further details of materials and general construction of constraining sleeves can be found in U.S. Pat. No. 6,352,561 to Leopold et al.

Figure 14:
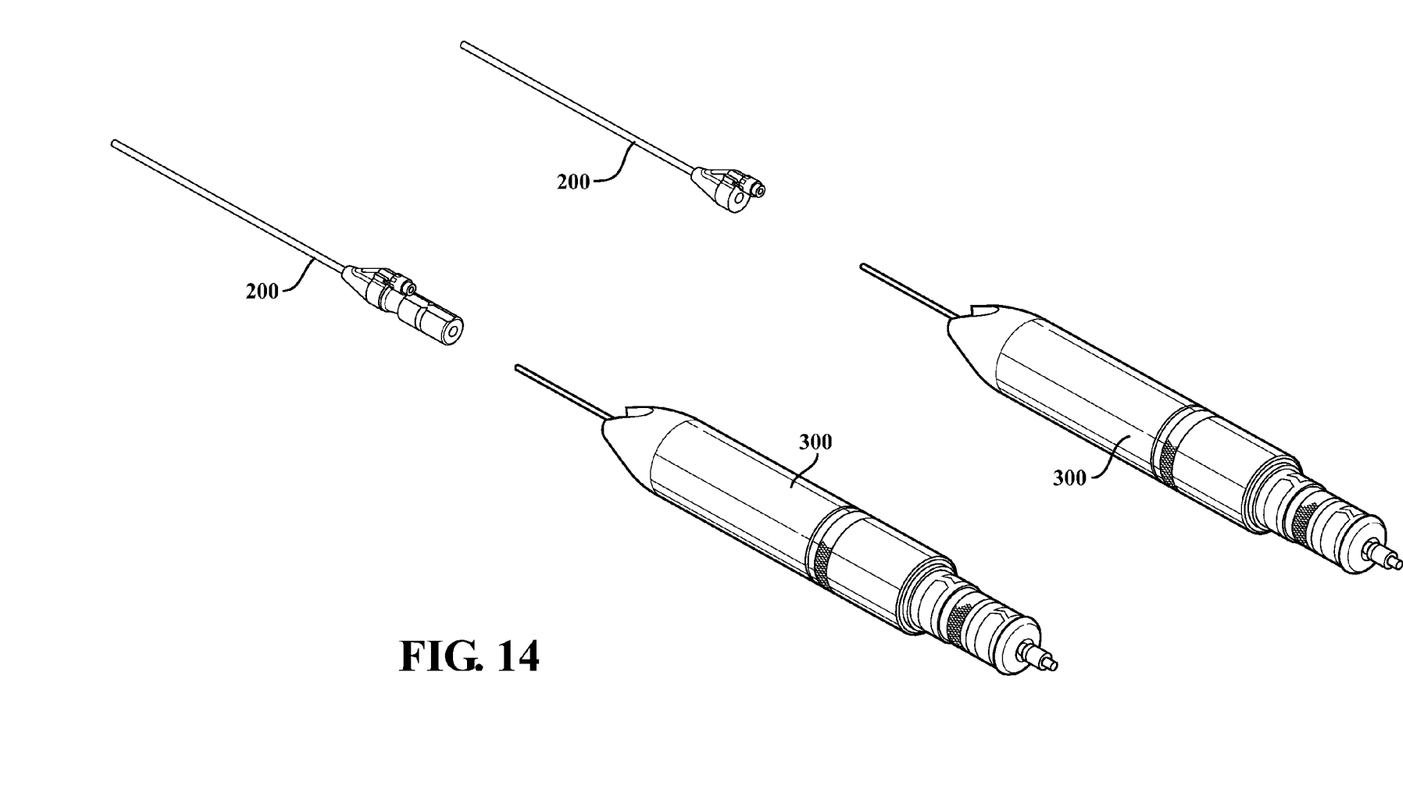
FIG. 14 illustrates perspective views of a handle and sheath of an introducer assembly decoupled from each other.

Referring to FIG. 14, the sheath 200 and handle 300 can be releasably coupled to each other for subsequent re-use of the sheath 200 as an introducer for other surgical implements after deployment of the device and de-coupling of the handle from the introducer. For example, the introducer and handle can be threaded or keyed with a slot-pin arrangement to form a releasable coupling that allows separation of the handle after deployment of the device and subsequent re-use or re-purposing of the introducer for introducing other surgical implements, such as other devices, tools, probes, cameras, drugs and saline.

It will be apparent to those skilled in the art that various modifications and variations can be made in the present disclosure without departing from the spirit or scope of the present disclosure. Thus, it is intended that the present disclosure cover the modifications and variations of this present disclosure provided they come within the scope of the appended claims and their equivalents.

What is claimed is:

1. A deployment handle for an introducer assembly, the handle comprising:
    a first actuating mechanism for actuating an implantable device deployment arrangement, the first actuating mechanism including a first helical guide, the implantable device deployment arrangement including a constraining sheath that is axially displaceable between a first state releasably constraining an implantable device toward a delivery configuration for endoluminal delivery and a second state allowing deployment of the implantable device;
    a second actuating mechanism for actuating a blocking arrangement between a first state in which access to one or more functions of the handle is blocked and a second state in which the access to one or more functions of the handle is unblocked; and
    a knob operatively coupled to both of the first and second actuating mechanisms to cause concurrent operation of both of the first and second actuating mechanisms in response to actuation of the knob, the first actuating mechanism being movable with the knob about a rotational axis.

2. The deployment handle as set forth in claim 1, wherein the first actuating mechanism includes a follower coupled to the constraining sheath and engaged with the first helical guide to cause axial displacement of the constraining sheath between the first and second states in response to corresponding rotation of the knob.

3. The deployment handle as set forth in claim 2, wherein the knob includes a receiving tube which can receive at least a portion of the constraining sheath therein as the constraining sheath moves between the first state and second state.

4. The deployment handle as set forth in claim 3, wherein the first helical guide comprises a first helical slot formed along an inner surface of the receiving tube.

5. The deployment handle as set forth in claim 4, wherein the follower includes a first pin engaged with the first helical slot.

6. The deployment handle as set forth in claim 1, wherein the blocking arrangement comprises a cover displaceable between the first state wherein the cover blocks the one or more functions of the handle and the second state wherein the cover is displaced from the first state to allow the access to the one or more functions of the handle.

7. The deployment handle as set forth in claim 6, wherein the cover and the constraining sheath move in opposite directions during actuation of the knob.

8. The deployment handle as set forth in claim 6, wherein the second actuating mechanism includes a second helical guide that translates rotation of the knob to axial displacement of the cover.

9. The deployment handle as set forth in claim 8 including a spindle about which the knob can rotate.

10. The deployment handle as set forth in claim 9, wherein the second helical guide comprises a second helical slot formed along an outer surface of the spindle, the second helical slot being axially aligned with the rotational axis of the knob.

11. The deployment handle as set forth in claim 10, wherein second actuating mechanism includes a longitudinal slot formed along one of the cover and the knob, wherein the slot is parallel with the rotational axis of the knob.

12. The deployment handle as set forth in claim 11, wherein the second actuating mechanism includes a second pin extending from the other of the one of the cover and the knob and engaged with the longitudinal slot to cause rotation of the cover with the knob during actuation of the knob.

13. The deployment handle as set forth in claim 12, wherein the second actuating mechanism includes a third pin extending from the cover and engaging the second helical slot to cause displacement of the cover between the first and second states in response to corresponding rotation of the knob.

14. A medical device deployment handle comprising:
    a first actuating mechanism for actuating a first implantable device deployment component;
    a first knob;
    a cover;
    a second actuating mechanism for actuating the cover relative to the second actuating mechanism and causing the deployment handle to transition from a first state in which the first knob is concealed by the cover to a second state in which the cover has been actuated such that the first knob is revealed, the first knob being distinct from the first and second actuating mechanisms and being configured to actuate a second implantable device deployment component; and
    a second knob operatively coupled to each of the first and second actuating mechanisms to cause concurrent actuation of both of the first and second actuating mechanisms in response to actuation of the second knob, the first and second knobs being independently actuatable such that the first and second knobs can be actuated relative to one another.

15. The deployment handle of claim 14, wherein the cover is displaceable relative to the first knob by actuating the second actuating mechanism.

16. The deployment handle of claim 14, wherein the cover is displaceable relative to the second actuating mechanism such that the cover conceals the first knob in the first state, and such that the cover is displaced in the second state to expose the first knob.

17. The deployment handle of claim 14, wherein the second knob is actuatable to cause the transition from the first state to the second state.

18. A deployment handle assembly comprising:
a constraining sheath;
a displacement member for retracting the constraining sheath from covering an implantable medical device;
a first knob for actuating a component of the handle assembly; and
a second knob that is actuatable to cause the handle to transition from a first state in which the first knob is inaccessible to a second state in which the first knob is accessible, the second knob being actuatable to cause the displacement member to retract the constraining sheath from covering the implantable medical device, the first and second knobs being independently actuatable such that the first and second knobs can be actuated relative to one another.

19. The deployment handle of claim 18, wherein actuation of the second knob causes the handle to transition from the first state to second state concurrently with causing the displacement member to retract.

20. The deployment handle of claim 18, wherein in the first state the constraining sheath covers and constrains the implantable medical device, and wherein in the second state the medical device is at least partially uncovered by the constraining sheath.

21. The deployment handle of claim 18, wherein the first knob is concealed in the first state and revealed in the second state.

* * * * *